United States Patent [19]

Lassen

[11] 4,205,671
[45] Jun. 3, 1980

[54] OUTFLOW DETECTOR AND CONTROL ARRANGEMENT

[75] Inventor: Per W. Lassen, Karup, Denmark

[73] Assignee: Kurt Ingvard Arnold Jaller, Denmark

[21] Appl. No.: 830,216

[22] Filed: Sep. 2, 1977

[30] Foreign Application Priority Data

May 16, 1977 [GB] United Kingdom ............... 20486/77

[51] Int. Cl.² ............................................... A61F 5/48
[52] U.S. Cl. ........................... 128/138 A; 128/419 R; 73/204; 324/65 R; 340/573; 340/604
[58] Field of Search ............... 128/2 R, 138 A, 138 R, 128/419 R, 419 S, DIG. 25, 630, 736; 73/204; 340/573, 584, 595, 618, 616, 602, 604; 324/65 R

[56] References Cited

U.S. PATENT DOCUMENTS

| | | | |
|---|---|---|---|
| 3,316,902 | 5/1967 | Winchel et al. | 73/204 X |
| 3,645,133 | 2/1972 | Simeth et al. | 73/204 |
| 3,942,515 | 3/1976 | Servos et al. | 128/2 R |

FOREIGN PATENT DOCUMENTS

| | | | |
|---|---|---|---|
| 97424 | 11/1963 | Denmark | 128/138 A |
| 2022538 | 11/1970 | Fed. Rep. of Germany | 73/204 |
| 7503935 | 10/1976 | Netherlands | 128/2 R |
| 680088 | 10/1952 | United Kingdom | 128/138 A |
| 146259 | 5/1961 | U.S.S.R. | 128/2 R |
| 198526 | 6/1967 | U.S.S.R. | 128/138 A |

*Primary Examiner*—Lee S. Cohen
*Attorney, Agent, or Firm*—Craig & Antonelli

[57] ABSTRACT

An arrangement for detecting and controlling an outflow which includes a temperature sensing device for sensing a temperature of the outflow and providing a signal of the detected temperature. A control arrangement is provided and is operatively associated with the temperature sensing device so as to effect a predetermined control operation upon the temperature sensing device providing a signal indicative of a predetermined temperature. The temperature sensing device may sense a temperature rise over a predetermined length of time or sense an increase in the temperature level.

17 Claims, 3 Drawing Figures

OUTFLOW DETECTOR AND CONTROL ARRANGEMENT

The present invention relates to a detector and control arrangement and, more particularly, to an arrangement for detecting an outflow from living bodies so as to, for example, detect and control or counteract nocturnal bed-wetting or general micturition. A large number of people suffer from enuresis which causes grave problems not only to the patients, but also to their families. To minimize the suffering and problems, it has been proposed to provide the patients with a detector device which includes spaced sensor electrodes held by underwear in an area adjacent a urethral orifice of the patient with the electrodes being connected in a circuit which is actuated in response to the establishment of electrical contact between said electrodes, which contact results, for example, from the presence of urine between the electrodes. The circuit, upon being actuated, initiates some suitable operation to counteract the micturition.

In some conventional micturition control devices, the operation to counteract the micturition simply consisted of switching on an electric bell or subjecting the patient to an electric shock which would be a sufficient stimulus to the patient so as to wake up a sleeping patient. While such devices have some controlling effect, the use often produces an adversion against such operation. Moreover, the reactions of both the patient and family often resulted in severe stress.

To somewhat alleviate the stresses resulting from the use of the above-noted conventional devices, Danish patent specification No. 97,424 proposes providing an arrangement wherein an electric shock for disturbing the patient was confined to a body region adjacent the ends of the nervus pudendus. By virtue of providing a perceivable electric shock adjacent the ends of the nervus pudendus, an automatic contracting of the annular closing muscle was caused since the electric shock stimulated the plexus vesicalis. The contracting of the annular closing muscle stops the urination as soon as it is detected and continued use of the arrangement gradually restores the natural function of the closing muscle.

While the last-mentioned arrangement was a great improvement over conventional devices, disadvantages thereof reside in the inconvenience associated with both the detection of an onset of micturition and the application of perceivable electric shocks with the latter being the most significant disadvantage to the patient for obvious reasons.

Further disadvantages of the detection of urine by spaced electrodes resides in the fact that such detection requires at least one of the electrodes to normally be held at some numeric electrical potential. Moreover, once a micturition is detected by a wetting of a pathway between said electrodes, the pathway will remain wet for a long period of time such as, for example, one-half hour after the first wetting, whereby a repeated wetting would not be detected.

A further micturition control device is proposed in U.S. Pat. No. 3,870,051 wherein the urinary control is achieved by way of electrical stimulation of the sphincter and bladder muscles effected by way of sacral ventral roots.

One disadvantage of the last-mentioned micturition control device resides in the fact that a portion of the device must be implanted into the body of the user.

A further disadvantage of the last-mentioned micturition control device resides in the fact that the control system is designed specifically for a dual mode operation; namely, a bladder hold mode and a bladder empty mode with the switching from one mode to the next being effected by way of a radio transmitter/receiver unit. Consequently, the proposed micturition control device is not readily adaptable to providing a control over involuntary micturition by an individual, but rather is designed for controlling disorders of a neurological origin and unless the control device is switched from a bladder hold to a bladder empty mode, an outflow would be prohibited, thereby adversely affecting the health of the user.

The aim underlying the present invention essentially resides in providing an improved arrangement for detecting and controlling an outflow such as, for example, micturition from a living body.

According to one feature of the present invention, a temperature sensing means is provided for sensing or detecting a temperature increase as caused by the outflow from a warm body rather than detecting an electric conductivity of a recipient of the outflow, as is the case with conventional devices. The use of a temperature sensing means for detecting an outflow from a living body is reliable since the immediate surroundings of a body are not normally as warm as the body itself, even if the human body is covered by blankets or other bed equipment.

One advantage of employing a temperature sensor at the place of occurrence of the urine or other outflow resides in the fact that the temperature sensor may be electrically fully insulated so as to present no open electric potential.

A further advantage of the use of a temperature sensor resides in the fact that the sensor is capable of sensing a renewed outflow rather soon after a previous outflow since the temperature of the matter in the first outflow will decrease immediately upon leaving the body and for a detection of a following outflow, it is immaterial whether the recipient is already wet.

Moreover, since the electric conductivity of a wetted area is not substantially changed by a temperature drop subsequent to an occurrence of urine or other outflow, a detection based on a measurement of increased conductivity between two spaced electrodes will not normally be useable for effecting any operation in case of repeated outflow. However, in accordance with the present invention, an outflow recipient may be provided which includes a material having a pronounced positive or negative temperature coefficient as far as its electric resistance or conductivity is concerned so that a temperature increase or decrease may be effected by the use of spaced electrodes.

In accordance with the present invention, when employed to detect micturition, a temperature sensing means is arranged at a urethral opening of an individual and provides an output signal of a detected temperature to a temperature rise detector which includes an appropriate circuit for producing an output signal as a function of a change of the signal from the temperature sensing means. The output signal of the temperature rise detector is fed to a temperature rise switch-over unit which is responsive to provide an output signal to a control gate in dependence upon a detected temperature rise. Upon the detected temperature rise reaching a predetermined value, the switch-over unit provides an output pulse to the gate so as to cause the same to activate a pulse shock generating means operatively connected to electrodes arranged at the nervus pudendus of the individual, thereby causing a contraction of a closing muscle.

By virtue of the advantageous features of the present invention, it is possible to control an operational effect of a detector arrangement in such a manner than an outflow is practically prevented or stopped not only upon a first occurrence, but each subsequent occurrence even when initial outflow moments are spaced by only a few seconds of time.

However, if a body tends to repeat initiation of an outflow, especially as far as urine is concerned, with time intervals of less than some three seconds, such repeat initiation is indicative of a real need of the body to effect an outflow; therefore, to effect stoppage of the outflow in response to repeat initiation of short time intervals would be dangerous to the body.

According to another feature of the present invention, the detector arrangement is preferably provided with a timer circuit which causes the detector arrangement to effect a counter operation against the outflow to be effectuated only if a predetermined time period of, for example, three seconds has lapsed since a foregoing outflow initiation. If the time period between outflow initiations is less than three seconds, it would be against the real need of the body to effect stoppage of the outflow and a free outflow would result.

It is also possible according to the present invention to detect an outflow by a temperature level rather than by a detection of a temperature increase. For this purpose, a thermoresistor is provided which is adapted to sense a predetermined temperature level of, for example 36° C. Upon a sensing of the predetermined temperature level, an output signal is provided to a control gate which, in turn, provides a signal to a pulse shock generating means connected to electrodes arranged at the nervus pudendus to cause a contraction of the closing muscle.

In order to preclude the thermoresistor from providing an erroneous output signal indicative of reaching a predetermined temperature level with a patient having a high fever, according to a still further feature of the present invention, a cooling means may be provided for controlling the temperature of the thermoresistor regardless of the body temperature of the patient. Alternatively, the thermoresistor may be adjustable by way of, for example, a switching means so as to shift the thermoresistor to a "high fever" range or by means of a body surface temperature sensor which automatically provides a necessary reference for defining a critical temperature, for example, one degree below a predetermined temperature.

Accordingly, it is an object of the present invention to provide an outflow detector and control arrangement which avoids by simple means the shortcomings and disadvantages encountered in the prior art.

Another object of the present invention resides in providing an outflow detector and control arrangement which is responsive to a temperature of the outflow and provides an appropriate corrective operation.

A still further object of the present invention resides in providing an outflow detector and control arrangement which functions reliably under all conditions.

Yet another object of the present invention resides in providing an outflow detector and control arrangement which minimizes any discomfort to a user.

Another object of the present invention resides in providing an outflow detector and control arrangement which is simple in construction and, therefore, inexpensive to manufacture.

These and other objects, features and advantages of the present invention will become more apparent from the following description when taken in connection with the accompanying drawings which show, for the purposes of illustration only, a single embodiment of the present invention which has been successfully tested on human beings, and wherein.

Figure 1:
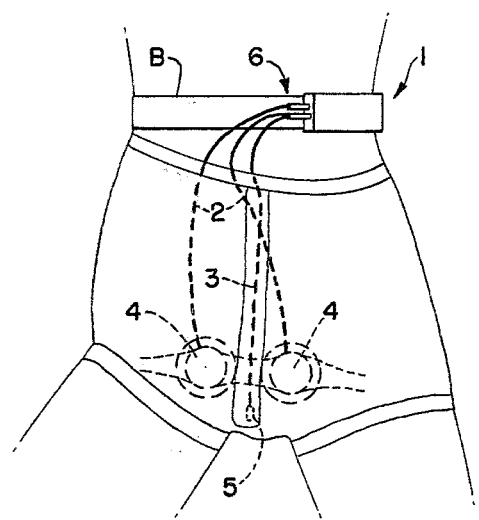
FIG. 1 is an outflow detector and control arrangement in accordance with the present invention attached to a user.

Referring now to the drawings wherein like reference numerals are used throughout the various views to designate like parts and, more particularly, to FIG. 1, according to this figure, the detector and control arrangement includes a function control unit generally designated by the reference numeral 1 which is adapted to be mounted on a body of a user by way of, for example, a belt B or the like. The function control unit 1 is operatively connected by suitable lead wires 2, 3 to a pair of electrodes 4 and a temperature sensor or feeler 5. For the sake of convenient attachment and removal from the body of the user, the lead wires 2, 3 are provided with suitable plug-type coupling or connecting elements generally designated by the reference numeral 6, which connect the electrodes 4 and temperature sensor or feeler 5 with the function control unit 1.

Figure 2:
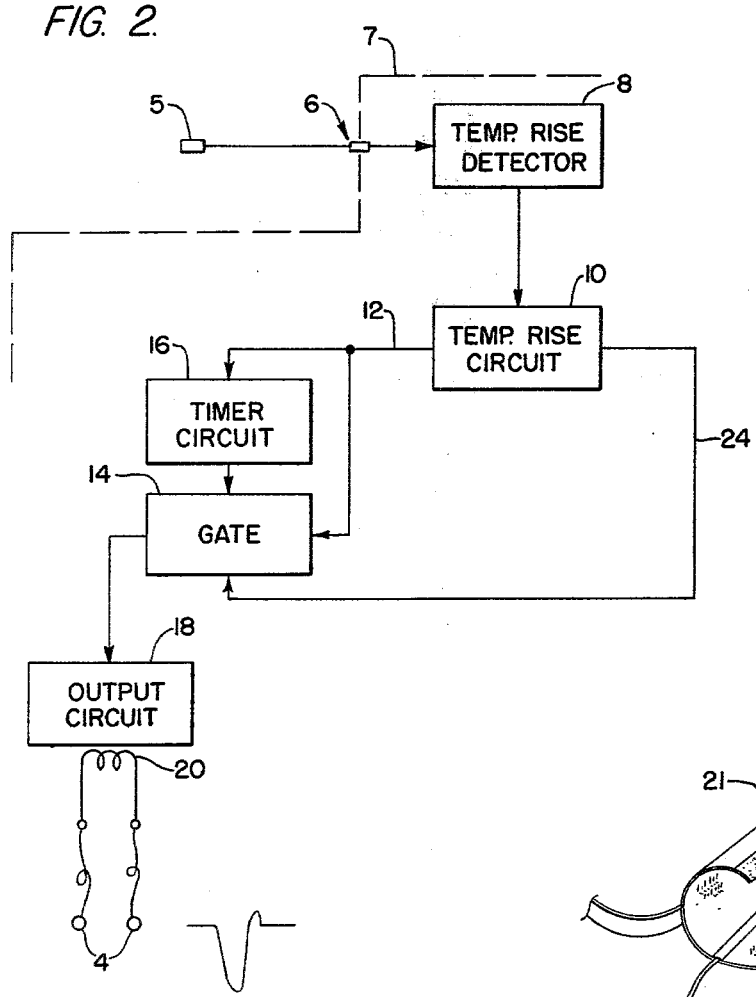
FIG. 2 is a schematic block diagram of the detector and control arrangement of FIG. 1.

As shown most clearly in FIG. 2, the function control unit 1 includes a housing 7 accommodating a temperature rise detector circuit 8, a gate or switch-over circuit 10, a timer circuit 16, a gate 14, and an output circuit 18 which includes a transformer 20, the secondary of which is connected to the electrodes 4 placed on the user's body, in a known manner, so as to provide a pulse shock to the nervus pudendus and thus cause a contraction of a closing muscle of the bladder to prevent an outflow or discharge from the body of the user.

The temperature sensor or feeler 5, arranged in the area of the urethral opening of the user, senses the tiniest drop of urine thereat and provides an output signal to the temperature rise detector circuit 8. The temperature rise detector circuit 8 provides an output signal as a function of the change of the signal from the sensor or feeler 5 to the gate or switch-over unit 10 which responds to a temperature rise of, for example, 1° C./sec., so as to provide through a "YES" wire or lead 12 a control pulse to the timer circuit 16 and gate 14.

The timer circuit 16 serves to open the gate 14 when a predetermined time period of, for example, three seconds has lapsed since a previous control pulse. If the gate 14 is open when a new control pulse for the gate or switch-over unit 10 arrives, then such pulse will pass to the output circuit 18 and transformer 20.

If the rate of the temperature rise is below 1° C./sec., or any other preferred limit, the gate or switch-over circuit 10 provides through "NO" wire 24 a control signal to the gate 14 so as to maintain the gate in a closed position.

According to experiments, the temperature rise limit of 1° C./sec. will secure the system against malfunctioning by a temperature rise caused by circumstances other than occurrence of the urine adjacent the temperature sensor or feeler 5 placed in any known or otherwise suitable manner immediately next to the urethral orifice. However, when the temperature rise is above said limit, the reaction time of the sensor 5 and the function control unit 1 need not even be one second from the initial urination.

The time delay control achieved by the timer circuit 16, for example, three seconds after a previous operation of the output circuit 18, is a special feature which serves to ensure that the closing muscle is not caused to be closed in a situation in which the body has a real need to release the urine for the detector and control arrangement would otherwise be injurious to the health of the patient.

By virtue of the utilization of the output transformer 20, it is ensured that the body electrodes 4 are galvanically separated from the remainder of the system, which is advantageous even in view of the fact that the thermosensor or feeler 5 need not have galvanic contact with the body and may be fully electrically insulated therefrom.

According to a further and important aspect of the present invention, the pulse control circuit 18 is designed and constructed so as to restrict the output pulse on the body electrodes 4 to a maximum of some 50 msec., whereby the closing muscle of the bladder is closed as desired without the pulse affecting the central nervous system. Thus, the patient or user will not feel the shock pulse as with prior art devices. This, of course, is significant when the detector and control arrangement is employed in connection with other conventional devices described hereinabove.

It will be appreciated that the use of a thermal detection principle provides significant advantages of its own without necessarily being connected with the resulting operation of the body electrodes 4 for urination control purposes. Thus, the thermal sensing by the feeler or sensor 5 would be applicable for controlling any other relevant operation, whether for urination control or other purposes and, for example, the sensor or feeler 5 may detect any type of warm outflow from a body, whether human or animal as would be the case with the birth of domestic animals. Moreover, the thermal detection may be used for providing an alarm signal or may effect other operations such as an operation serving to counteract or even to promote an action which has given rise to the detection.

Figure 3:
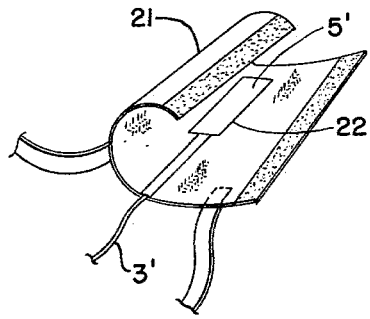
FIG. 3 is a perspective view of an outflow recipient in accordance with the present invention adapted for use by males.

As far as urination control is concerned, it has been a problem to arrange a sensor means in underwear in a well defined position adjacent the urethral orifice of boys and men because of the normal small size of their penis. However, in accordance with the present invention, as shown most clearly in FIG. 3, a sensor holder is provided and fashioned as a textile sheet 21 to be wrapped about a penis with the sheet 21 being prepared along its opposed edge portions to be closable by means of a so-called overlapping burr closure so that it is adaptable to any thickness of the penis. The textile sheet 21 is provided with a channel or pocket portion 22 into which may be introduced the sensor wire 3' and thermal sensor or feeler 5', thereby providing a well defined location of the head of the sensor or feeler 5' adjacent the outer end of the wrapping member in proximity to the urethral opening.

It is also possible in accordance with the present invention to provide an arrangement which senses a predetermined temperature level rather than a predetermined temperature rise in an outflow. Thus, for example, a thermoresistor device (not shown) may be arranged at a urethral opening for sensing a predetermined temperature level of, for example, 36° C., with the thermoresistor device providing a signal to a control gate upon the device sensing a temperature in excess of the predetermined temperature level. The gate in turn permits a pulse shock to be provided to the electrodes so as to cause a contraction of the closing muscles of the bladder.

As readily apparent, the schematic diagram of FIG. 2 provides only one possible detector and control circuit arrangement and additional modifications are possible so long as the output pulse is conditioned by a detected temperature rise or a detected temperature level.

To provide for a relatively long life of the detector and control arrangement, the function and control unit 1 is one hundred percent transistorized and works directly on a dry cell battery. By virtue of the fact that the unit is completely transistorized, the current consumption is minimal and the arrangement has an effective power time of 200 to 500 hours.

While I have shown and described only one embodiment in accordance with the present invention, it is understood that the same is not limited thereto, but is susceptible of numerous changes and modifications as would be known to those skilled in the art, and I therefor do not wish to be limited to the details shown and described herein, but intend to cover all such changes and modifications as are encompassed by the scope of the appended claims.

I claim:

1. An arrangement for detecting and controlling an outflow, the arrangement comprising: means for sensing a temperature of the outflow and for providing a signal of a detected temperature, and means responsive to the signal of the detected temperature for effecting a predetermined control operation upon said sensing means providing a signal indicative of a predetermined temperature, wherein said temperature sensing means including a sensor element adapted to be disposed in an area of the outflow so as to sense a rise in temperature over a predetermined length of time, wherein said means for effecting a predetermined control operation includes a detector means operatively connected with said sensor element, and a temperature rise circuit means operatively connected with said detector means for providing a control pulse upon said detector means detecting a predetermined temperature rise, wherein said means for effecting a predetermined control operation includes an output circuit means for providing a control stimulus pulse in response to a control pulse from said temperature rise circuit means, and a gate means for controlling an activation of said output circuit means is interposed between said temperature rise circuit means and said output circuit means.

2. An arrangement according to claim 1, wherein a timing circuit means is interposed between said temperature rise circuit means and said gate means for controlling an operation of said gate means upon a lapse of a predetermined time interval between control pulses from said temperature rise circuit means.

3. An arrangement according to claim 2, wherein the output circuit means includes a transformer and a pair of electrode means operatively connected to a secondary of the transformer for applying the control stimulus pulse in the form of a control shock pulse.

4. An arrangement according to claim 3, wherein the control shock pulse has a maximum duration of about 50 milliseconds.

5. An arrangement according to claim 3, wherein the outflow is urine, said sensor element is adapted to be arranged and disposed in an area of a urethral opening, said electrode means are adapted to be disposed in an area of nervus pudendus so that the control shock pulse is applied to the nervus pudendus to cause a closing of a muscle of a bladder.

6. An arrangement according to claim 5, wherein means are provided for mounting the sensor element in the area of the urethral opening.

7. An arrangement according to claim 6, wherein said mounting means includes a textile sheet of material adapted to be disposed about a male organ, and means are provided on said textile sheet of material for accommodating said sensor element so as to be disposed in the area of the urethral opening.

8. An arrangement according to claim 1, wherein the output circuit means includes a transformer and a pair of electrode means operatively connected to a secondary of the transformer for applying the control stimulus pulse in the form of a control shock pulse.

9. An arrangement according to claim 8, wherein the outflow is urine, said sensor element is adapted to be arranged and disposed in an area of a urethral opening, said electrode means are adapted to be disposed in an area of nervus pudendus so that the control shock pulse is applied to the nervus pudendus to cause a closing of a muscle of a bladder.

10. An arrangement according to claim 9, wherein means are provided for mounting the sensor element in the area of the urethral opening.

11. An arrangement according to claim 10, wherein said mounting means includes a textile sheet of material adapted to be disposed about a male organ, and means are provided on said textile sheet of material for accommodating said sensor element so as to be disposed in the area of the urethral opening.

12. An arrangement according to claim 11, wherein the control shock pulse has a maximum duration of about 50 milliseconds.

13. Micturition detection and control apparatus comprising: a temperature sensing means for detecting the presence of a substance of a predetermined temperature and for producing a signal in response thereto, and control means for performing a micturition control operation in response to said signal, wherein said temperature sensing means includes a thermoresistor means adapted to be disposed in an area of fluid outflow for measuring a temperature level of the outflow and for providing an output signal indicative of the measured temperature level, and wherein said signal responsive control means includes control shock pulse generating means operatively connected with said thermoresistor means for providing a control shock pulse upon said thermoresistor means measuring a predetermined temperature level, wherein a gate means is interposed between said thermoresistor means and said control shock pulse generating means for controlling an activation of said control shock pulse generating means, and wherein said control shock pulse generating means includes a pair of electrode means for applying the control shock pulse.

14. An arrangement for detecting and controlling an outflow, the arrangement comprising: means for sensing a temperature of the outflow and for providing a signal of a detected temperature, and means responsive to the signal of the detected temperature for effecting a predetermined control operation upon said sensing means providing a signal indicative of a predetermined temperature, wherein said temperature sensing means includes a thermoresistor means adapted to be disposed in an area of fluid outflow for measuring a temperature level of the outflow and for providing an output signal indicative of the measured temperature level, and wherein said signal responsive control means includes control shock pulse generating means operatively connected with said thermoresistor means for providing a control shock pulse upon said thermoresistor means measuring a predetermined temperature level, wherein a gate means is interposed between said thermoresistor means and said control shock pulse generating means for controlling an activation of said control shock pulse generating means, wherein said control shock pulse generating means includes a pair of electrode means for applying the control shock pulse, wherein the outflow is urine, said thermoresistor means is adapted to be arranged and disposed in an area of a urethral opening, said electrode means are adapted to be disposed in an area of nervus pudendus so that the control shock pulse is applied to the nervus pudendus to cause a closing of a muscle of a bladder.

15. An arrangement according to claim 14, wherein means are provided for mounting the thermoresistor means in the area of the urethral opening.

16. An arrangement according to claim 15, wherein said mounting means includes a textile sheet of material adapted to be disposed about a male organ, and means are provided on said textile sheet of material for accommodating said thermoresistor means so as to be disposed in the area of the urethral opening.

17. An arrangement according to claim 16, wherein the control shock pulse generating means includes a transformer and said pair of electrode means operatively connected to a secondary of the transformer for applying the control shock pulse.

* * * * *